United States Patent [19]

Drukier

[11] Patent Number: 4,618,773

[45] Date of Patent: Oct. 21, 1986

[54] APPARATUS FOR THE DIAGNOSIS OF BODY STRUCTURES INTO WHICH A GAMMAEMITTING RADIOACTIVE ISOTOPE HAS BEEN INTRODUCED

[76] Inventor: Andrej K. Drukier, c/o H. Hessel, 532 W. 111th Apt. 76, New York, N.Y. 10025

[21] Appl. No.: 538,794

[22] Filed: Oct. 4, 1983

[30] Foreign Application Priority Data

Oct. 4, 1982 [GB] United Kingdom ............... 8228232

[51] Int. Cl.[4] ............................................. G01T 1/164
[52] U.S. Cl. ............................... 250/363 S; 250/367; 250/374; 250/394
[58] Field of Search .................. 250/363 S, 367, 394, 250/370 E, 370 G, 370 GX, 370 H, 370 I, 486.1, 385 R, 374; 378/7

[56] References Cited

U.S. PATENT DOCUMENTS

| | | |
|---|---|---|
| 3,581,087 | 5/1971 | Brinkerhoff et al. ............... 250/393 |
| 4,247,774 | 1/1981 | Brooks .............................. 250/367 |

FOREIGN PATENT DOCUMENTS

| | | |
|---|---|---|
| 2377643 | 8/1978 | France . |
| 2377642 | 8/1978 | France ............................. 250/363 S |
| 958240 | 5/1964 | United Kingdom ................ 250/385 |

OTHER PUBLICATIONS

A. Schmitt, H. Fessler, "Recent Developments in Lung Counting of Transuranium Nuclides at Karlsruhe" Conference: Proceedings of an International Seminar on Diagnosis and Treatment of Radionuclides, Vienna, Austria (8–12 Dec. 1975) pp. 285–292.

H. Zaklad, S. Derenzo, R. Muller, G. Smadja, R. Smits, L. Alvarez, "A Liquid Xenon Radioisotope Camera" IEEE Trans. Nucl. Sci. vol. NS-19, No. 3 (Jun. 1972) pp. 206–213.

Primary Examiner—Alfred E. Smith
Assistant Examiner—Constantine Hannaher
Attorney, Agent, or Firm—Townsend & Townsend

[57] ABSTRACT

Body structures into which a gamma-emitting isotope has been introduced are investigated using an imaging system comprising in sequence a collimator, a first detector, a filter, and a second detector. The first detector is partially transparent to the emerging photons and the filter is adapted to have an absorption edge energy fractionally less than the energy of the radioactive isotope source. The first detector produces an image of both scattered and non-scattered photons and the second detector simultaneously produces an image of only the scattered photons. The two images can be manipulated to produce an image due only to non-scattered photons which is the image of interest.

14 Claims, 5 Drawing Figures

PLOT FOR Pb

APPARATUS FOR THE DIAGNOSIS OF BODY STRUCTURES INTO WHICH A GAMMAEMITTING RADIOACTIVE ISOTOPE HAS BEEN INTRODUCED

The present invention relates to apparatus for the diagnosis of body structures into which a gamma-emitting radioactive isotope has been introduced.

Gamma detectors and associated collimators are used in nuclear medicine to study the morphological and/or physiological changes in biological organisms. The best possible spatial resolution is required to study objects within an organism, such as a cancer tumor, as small as a few millimeters in size.

One of the serious limitations to the spatial resolution of detectors in current use is due to the scattering of photons on the electrons of the organism, known as Compton scattering. Scattered photons are deflected and may be misinterpreted as if they were emitted in another part of the body. This distortion leads to decrease of image contrast and to the creation of artifacts, which are details or structures present in the image but having no counterpart in the organism. Therefore, for accurate diagnosis, the scattered photons should be eliminated when the image is reconstructed. The cross-section for Compton scattering decreases with energy and therefore only those radioisotopes with energies above 70 keV are usually used.

When scattered, photons loose part of their energy. In order to reject the scattered photons during the image reconstruction, it is essential to use quasi-monochromatic sources of gamma radiation and photon detectors with very good energy resolution. While the radioactive gamma sources are essentially monochromatic, the energy resolution of most presently available photon detectors is poor; for example, NaI scintillators have an energy resolution of 15–20%. Only the semiconductor detectors have an energy resolution of better than 10%, but they have the disadvantage of being much more expensive.

In my French patent application No. 77 01150 published as Pat. No. 23 77 642 I have proposed a new nuclear medical imaging arrangement which allows a significant improvement in energy resolution ($\Delta E/E \leq 5\%$). This improvement is obtained by the use of detectors comprised of elements of high atomic number (but thinner than those hitherto proposed, with the high atomic number element's being selected to have an absorption edge energy slightly below the radiation energy of the gamma-emitting radioisotope which is to be detected.

In my French patent I have also proposed a way of improving the images obtained with existing detectors used in nuclear medical imaging, such as the NaI scintillation camera. This is achieved by the use of filters of high atomic number materials in conjunction with energymatched gamma-emitting isotopes. This enables an image to be formed substantially only of photons which are emitted from the isotope within the tissue and scattered by the tissue. A further image can also be formed in the normal way without the filter and this further image can be considered to be a composite of the undesired false image due to photons scattered within the tissue, superimposed on the real image representing the distribution of the photon emitters inside the tissue. A mathematical procedure permits the image due to scattered photons to be subtracted from the composite image, thereby obtaining the real image.

However, with this technique two images have to be formed at different times which is disadvantageous (possibility of movement of the patient so that the two images are not truly coincident period of time required etc.).

The principal object underlying the present invention is to provide an improved nuclear medical imaging arrangement and method which avoids the need to form a plurality of images at different times, which yields improved images and facilitates interpretation of these images.

In order to satisfy this object there is provided, in accordance with the present invention, apparatus for the diagnosis of body structures into which a gamma-emitting radioactive isotope has been introduced, the apparatus comprising, in sequence, a collimator through which photons emanating from the body structures being studied are directed; a first photon detector, said first photon detector being adapted to absorp a fraction of the photons incident thereon; a filter comprising an element with an atomic number not less then 74; a second photon detector for detecting photons passing through said filter and analysing means for producing an image due to non-scattered photons from the image of scattered photons formed by the second detector and the image of scattered and nonscattered photons formed by the first detector.

Thus two detectors are used, with a heavy element filter interposed between them, so that two images—one that of the scattered photons alone and the other a composite of the real and false images—may be obtained simultaneously. The true image of the photons emanating from within the tissue is obtained from these two images (for example, by selecting upper and lower scintillator detectors of differing pulse decay times and utilizing suitable electronic circuitry). The arrangement results in good energy resolution and the images are obtained in a much more efficient manner.

Further advantageous arrangements are set out in the accompanying subclaims.

The invention will now be described in more detail by way of example only and with reference to the accompanying drawings, and tables, in which.

Table 1 shows the absorption edge energies of certain elements with atomic number Z greater or equal to 74. The following quantities are of interest and are listed in Table 1:

$\mu_+$—absorption coefficient just above $E_a$, $\mu_-$—absorption coefficient below $E_a$,
$\mu_{15\%}$—absorption coefficient at $E=0.85\times E_a$.

Table 2 is a listing of radioactive isotopes tabulated against the suitable very high atomic number element from which the filter should be built.

Before describing the specific arrangement of the present invention it is considered helpful to discuss the underlying theory and the arrangements proposed in my French patent.

Figure 2:
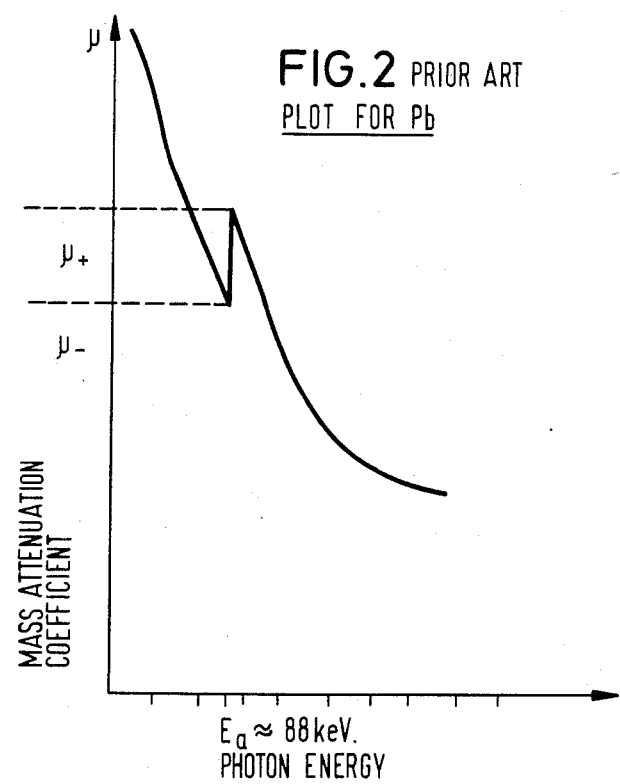
FIG. 2 is a plot of the mass attenuation coefficient for lead versus photon energy, illustrating the typical absorption edge energy.

It is well known that the mass absorption coefficient of an element increases drastically at some characteristic energy (see FIG. 2 for lead). The absorption edge energy is between a few keV for low atomic number elements and as high as 115 keV for Uranium, i.e. it increases for higher atomic numbers. In medical applications, photons of low energy have only a relatively small chance of escaping from the organism and only the highest Z elements can be considered as radiation detectors or filters. The absorption edge energies for some elements with $Z \geq 74$ are listed in Table 1. Elements like Re, Os, Ir, or the actinides different than Uranium are omitted because they are prohibitively expensive.

The possibility of improving the energy resolution of existing photon detectors results from the existence of gamma emitters with energies slightly above the absorption edge energy of corresponding detector materials (see Table 2). Only isotopes with a decay life longer than 10 minutes are listed and then only the energy, $E_{gamma}$, of radiation close to the absorption edge of interest is included, even if these radioisotopes are not monochromatic.

Table 2 shows the decay time (half life time $t_{\frac{1}{2}}$), the isotope energy $E_{gamma}$, and the relative interval between $E_{gamma}$ and the absorption edge $E_a$. The last column of table 2, lists the element whose absorption edge is closest to the energy of the radioisotope. This element with atomic number Z is ideal for use as heavy detector or filter. However, also elements with Z-1 and Z-2 can be used to reject scattered photons.

Figure 1:
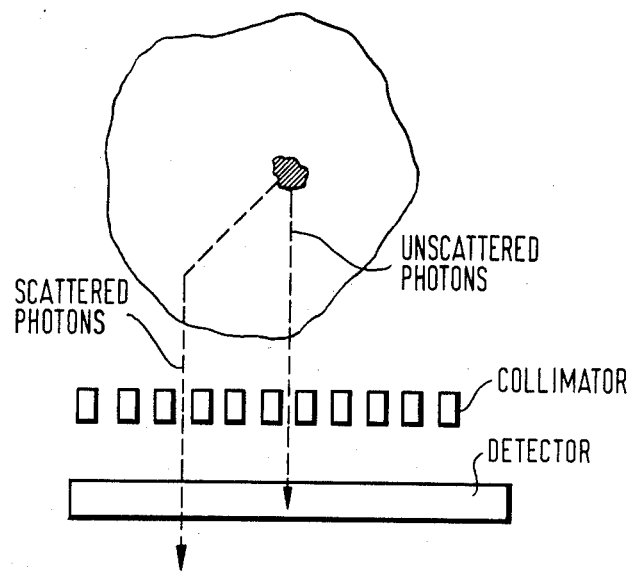
FIG. 1 shows schematically a first detector configuration using a thin very high atomic number detector as proposed in my French patent.

FIG. 1 shows one arrangement proposed in my French patent, the layout of the apparatus does not differ from the classical arrangement.

The collimator is transparent to photons propagating in the chosen direction only. It makes it possible to obtain a two-dimensional (2-D) projection of the 3-D object under study. The collimator is usually realised as a "multihole collimator", i.e. a thick sheet of metal in which holes have been made. The collimator is a device well known in the prior art and will therefore not be discussed in the following. For an arbitrary detector, or if the source has an energy considerably higher than the absorption edge energy, both the "true", i.e. unscattered and the "false", i.e. the scattered photon will be absorbed inside the detector. Actually, the probability of absorbing a false photon is higher than that of absorbing a "true" photon. For example, for the most popular radioisotope $Tc^{99m}$ for which $E_{gamma}=140$ keV and a detector consisting of pure lead, $E_a=88$ keV, we have $\mu(E=140 \text{ keV})=2.27 \text{ g/cm}^2$, whereas for photons scattered through an angle of 45° we have $u(E=127 \text{ keV})$, $=3.84 \text{ gm/cm}^2$. The differences in absorption coefficient is generally inadequate for rejection of the scattered photons.

Drastically different is the situation for the very particular cases when the energy of an emitted photon is very close to the absorption edge of a detector of appropriate thickness (as proposed in my French patent). Almost all scattered photons will have energies below the absorption edge and the mass absorption will be very small. For the sake of simplicity, let us assume that the filter consists of a pure, very high atomic number element. With an appropriate thickness of the filter, almost all, say 90% of "true" photons will be stopped, but almost all scattered photons will pass through the filter. This difference will be lost if the detector is too thick, that is to say that the filter should be thinner than 5 gm/cm$^2$.

Figure 3:
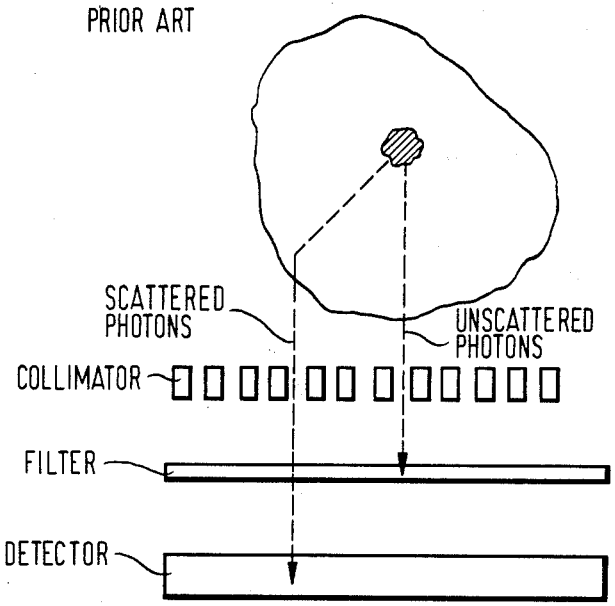
FIG. 3 shows schematically a second detector configuration as proposed in my French patent and employing a conventional detector, with a removable thin, very high atomic number filter interposed between the organism being scanned and the detector.

FIG. 3 shows the alternative arrangement proposed in my French patent. Here a high atomic number filter $Z \geq 74$, matched to the emission energy of the isotope is removably interposed between the collimator and the detector. A first image F due mainly to scattered photons is obtained with the filter in position. The filter is removed and a second image NF is obtained, this time of the scattered and non-scattered photons. The true desired image of the non-scattered photons is then obtained by mathematical techniques. The first image F is, in effect, used to correct the second image NF.

Let us assume that in the image obtained without filter the fraction of scattered photons is $\beta$ (usually 20–50%). To account for the scattered photons, the filter should have an appropriate thickness. If the filter is too thin, some of the unscattered photons will pass through it. This can lead to the creation of artifacts when the image is reconstructed. For a filter of thickness x, the transmissivities for scattered and unscattered photons are $t_1 = \exp-(\mu_- x)$ and $t_2 = \exp(\mu_+ x)$, respectively. It can be shown that in an image obtained with the filter, the fraction b of non-scattered photons is $$b = (1-a)/((t_1/t_2)*a + 1)$$

where a is the average fraction of photons scattered inside the body. The fraction b should be small, say $b \leq b_0$ and $$x \geq \ln((1-a)*(1-b_0)/(a*b_0))/(\mu_+ - \mu_-).$$

For example, with $b_0 = 10\%$, $a = 10\%$ and the thickness of a lead filter should be $x \geq 0.48$ g/cm$^2 \approx 0.42$ mm. On the other hand, if the filter is too thick, a portion of the scattered photons will be stopped. Thus the time necessary to obtain the correction matrix will be longer, or the irradiation dose must be higher.

In the following capital letters will be used for the matrix representations of images. Furthermore, the asterisk "*" is used when the matrix is multiplied by a scalar or other matrix. The following matrices are of interest:

I—real distribution of radioisotope inside studied biological object;
NS—image of the object when all scattered photons are rejected ("signal");
S—image of the object when only scattered photons are accounted for ("noise");
NF—image obtained without the filter;
F—image obtained with filter;
R—reconstructed image.

The matrix A can be defined in the following way:
NF=NS+S
F=t$_1$*S+t$_2$*NS
NS=(1−A)*I
S=A*I where $t_1 \approx \exp{-(\mu_-x)}$ and $t_2 \approx \exp{-(\mu_+x)}$ are the transmissivities of the filter for scattered and unscattered photons, respectively. However, tests have shown that good reconstruction can be obtained when the matrix A is replaced by the scalar fraction a. For a given radioisotope, a can be estimated from a knowledge of the anatomy of the studied person. For radioisotopes with $E_{gamma}$=80-120 keV, a=10-40% for all organs with exception of the thyroid. Thus the optimum reconstruction is: $I=(F-t_1 *NF)/((t_2-t_1)(1-a))_2$. For example, for a Pb filter $t_1=52\%$ and 27% for x=0.5 and 1 g/cm² respectively. Thus the filter thickness should be between 0.25 g/cm² and 1.0 g/cm².

Filters can be built of pure, very high atomic number elements or their compounds. In the following, the term "equivalent thickness of the filter" is used, which gives the thickness of only the very high Z elements in units g/cm² inside the filter. As the other components of the filter are supposed to be of low Z their absorption coefficients are negligible even if their contribution to the weight is considerable.

In practice the arrangement of FIG. 1 is something of a compromise and the arrangement of FIG. 2 results in the need to form two images at different times with the aforementioned disadvantages, particularly movement of the patient during data acquisition.

Figure 4:
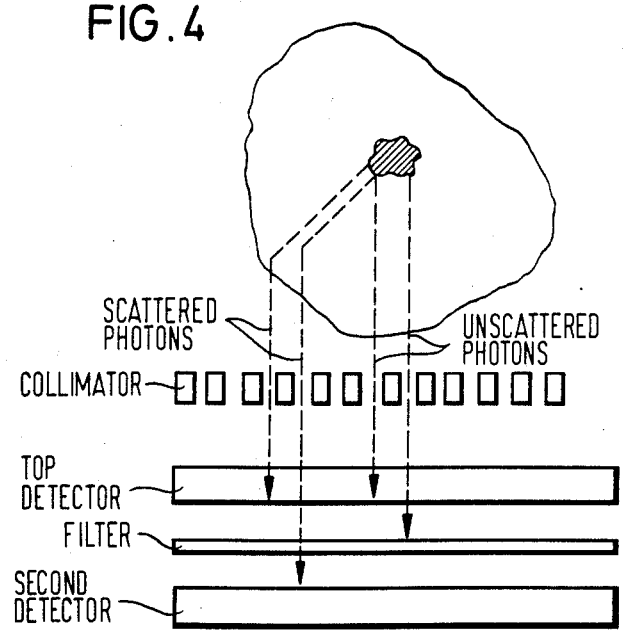
FIG. 4 illustrates schematically the arrangement of the present invention which uses two detectors with a filter interposed between them.

The present invention is, as already indicated directed to an arrangement which overcomes this difficulty. The arrangement of the invention makes use of two detectors separated by an appropriate filter as shown in FIG. 4.

The top detector, closer to the patient, should be transparent, i.e. only 10-50% of the available photons should be stopped therein. More specifically, it is proposed to use a Xe multiwire proportional chamber as the top detector, and the Anger camera (Na I scintillator) as the second detector. The Xe detectors have very good intrinsic spatial resolution, <1mm, and a reasonable energy resolution, $\Delta E/E \approx 20$-25% at 100 keV. However, they are partially transparent for photons with $E_{gamma} \geq 50$ keV. This normally severely limits the use of gas detectors in nuclear medicine. In the disclosed embodiment of FIG. 4, however, the top detector should be transparent, and thus it is very convenient to use Xe as the top detector.

Another class of photon detectors with excellent spatial resolution and reasonable energy resolution are detectors based on the liquid noble gases, e.g. liquid argon and liquid xenon. Thus the top detector of FIG. 4 may also be a thin, liquid noble gas detector.

Figure 5:
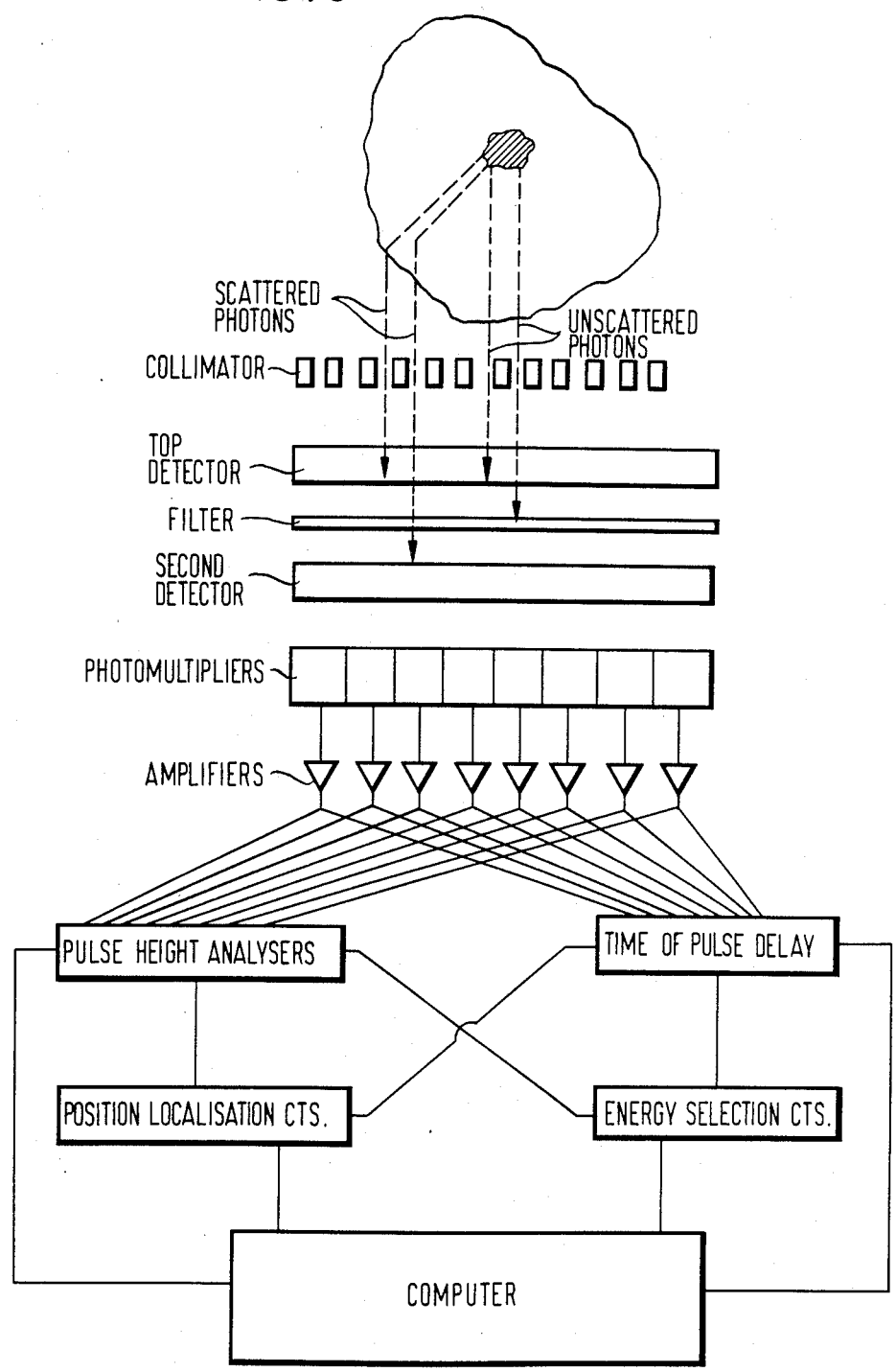
FIG. 5 illustrates in diagrammatic form the use of two scintillation crystals separated by an optically transparent filter combined with electronic circuit means for processing the signals produced by photon detection.

The FIG. 5 embodiment uses a fast scintillator, such as CsI, BaF, CsF or plastic scintillator, as the top detector and an appropriate filter to improve the imaging capabilities of the existing Anger camera. I.e. two different scintillators, separated by an appropriate filter, are used.

With this arrangement a transparent filter, e.g. a heavy metal loaded glass or plastic is necessary because the use of an opaque filter would mean that both the top and bottom scintillator would have to be provided with a separate set of photomultipliers which would drastically impair the imaging capability. The use of a transparent filter brings the special benefit that only one set of photo-multipliers is required. Of course it is necessary for the single set of photomultipliers to be able to distinguish between photons stopped in the top and bottom scintillators respectively. This can be done conveniently by using a fast scintillator such as cesium iodide as the top detector and a slow scintillator such as NaI as the bottom detector. The inverse situation is also possible but not so convenient because of differences in stopping power.

By way of example the pulse delay time of CsI=60 nsec. whereas NaI=240 nsec., and circuits exist which can analyze the time of pulse decay. Thus,it is possible to determine whether the gamma was stopped in the top (fast) scintillator or in the NaI crystal below the filter. This technique is well known—it is called phoswitch—but has never been used for position sensitive detectors. Furthermore, the use of an optically transparent filter based on very high atomic number elements and placed between the two elements of a phoswitch detector is entirely novel. In existing phoswitch detectors, the thickness of both fast and slow crystals is arbitrary. It should be noted that to practise this invention, the thickness of both the top detector and the filter must be chosen in accordance with this disclosure, whereas the thickness of the bottom detector is not critical.

The functions of the electronic modules in FIG. 5 can be realised using prior art devices. The signals from the photomultipliers are first amplified.

The signals from the amplifiers go to pulse height analysers, such as analogue to digital converters and are then passed to position localisation circuits which are essentially the same as in existing Anger cameras and which identify the positions at which the photons are absorbed. This information is passed to the computer.

In addition the output of the pulse height analysers is passed to the energy selection modules which analyse the intensity of the individual scintillators and thus the energy of the absorbed photons. This information is also passed to the computer. It will be appreciated that the operation of the position localisation circuits and the energy selection circuits depends crucially on the scintillator in which scintillation occurred,this information is provided by time of pulse decay modules.

The time of pulse decay can be realised using a time-to-digital converter or, alternatively using constant delay and coincidence circuits. However, it should be pointed out that light emission from the fast scintillator is smaller than from the NaI crystal. Thus, if the energy selection circuit is the same for both detectors, the photons absorbed in fast scintillator may be misinterpreted as the scattered photons detected in NaI. Thus a crucial element of the present invention is the presence of the interconnections between the pulse decay modules and the position localisation and energy selection modules.

Furthermore all the information is stored in the computer, which may be a microprocessor, for subsequent off-line analysis.

The computer also produces the resultant real image from the information it receives, i.e. using the matrix analysis previously described.

TABLE 1

|   | Z | $E_a$ | $u_+$ | $u_-$ | $u_{15\%}$ |
|---|---|---|---|---|---|
| W | 74 | 69.51 | 11.4 | 2.55 | 3.7 |
| Pt | 78 | 78.38 | 9.62 | 2.09 | 3.2 |
| Au x | 79 | 80.67 | 8.53 | 1.42 | 2.5 |
| Hg x | 80 | 83.08 | 8.23 | 1.38 | 2.4 |
| Tl | 81 | 85.52 | 7.93 | 1.34 | 2.3 |
| Pb | 82 | 85.52 | 7.63 | 1.30 | 2.15 |
| Bi x | 83 | 90.54 | 7.33 | 1.26 | 2.1 |
| U | 92 | 115.0 | 4.79 | 0.865 | 1.3 |

$E_a$ in keV; $u_+$, $u_-$, $u_{15\%}$ in g/cm²
X $u_+$, $u_-$, $u_{15\%}$ calculated by extrapolation.

TABLE 2

| | $t_{\frac{1}{2}}$ | $E_\gamma$ keV | $(E_\gamma - E_a)/E_a$ | |
|---|---|---|---|---|
| Ir$^{193}$ | 11 d | 69.5 | ? | W |
| Sm$^{153}$ | 47.1 h | 69.8 | 0.4% | W |
| Gd$^{153}$ | 236 d | 69.8 | 0.4% | W |
| Co$^{61}$ | 99 m | 70 | 0.7% | W |
| Cu$^{61}$ | 3.3 h | 70 | 0.7% | W |
| Ge$^{66}$ | 2.5 h | 70 | 0.7% | W |
| Ba$^{133}$ | 7.2 y | 70 | 0.7% | W |
| Pm$^{151}$ | 27.5 h | 70 | 0.7% | W |
| Lu$^{177}$ | 6.8 d | 71.6 | 2.9% | W |
| Os$^{185}$ | 93.6 d | 71.6 | 2.9% | W |
| Pm$^{145}$ | 18 y | 72 | 3.5% | W |
| W$^{187}$ | 24.0 d | 72 | 3.5% | W |
| Ge$^{77}$ | 11.3 h | 73 | 4.8% | W |
| Ho$^{164}$ | 36.7 m | 73 | 4.8% | W |
| U$^{239}$ | 23.5 m | 73.6 | 5.6% | W |
| Au$^{193}$ | 15.8 h | 73.7 | 5.7% | W |
| Sr$^{83}$ | 33 h | 74 | 6.0% | W |
| Gd$^{161}$ | 3.6 m | 78 | 6.8% | W |
| Bi$^{204}$ | 11.6 h | 78.5 | 0.15% | Pt |
| Lu$^{173}$ | 1.4 y | 78.8 | 0.53% | Pt |
| Ce$^{144}$ | 285 d | 79.9 | 1.9% | Pt |
| Tm$^{168}$ | 85 d | 79.9 | 2.0% | Pt |
| Mo$^{101}$ | 14.6 m | 80 | 2.1% | Pt |
| I$^{131}$ | 8.1 d | 80 | 2.1% | Pt |
| Pr$^{145}$ | 22 m | 80 | 2.1% | Pt |
| Eu$^{147}$ | 24 d | 80 | 2.1% | Pt |
| Ho$^{166}$ | 27.3 h | 80 | 2.1% | Pt |
| Ir$^{193m}$ | 11.9 d | 80.2 | 2.3% | Pt |
| Pd$^{100}$ | 4.0 d | 80.7 | 2.9% | Pt |
| Pd$^{100}$ | 4.0 d | 80.7 | ? | Au |
| Se$^{75}$ | 127 d | 80.8 | 0.11% | Au |
| Ea$^{223}$ | 11.3 d | 80.9 | 0.23% | Au |
| Ee$^{133}$ | 5.27 d | 81 | 0.33% | Au |
| Ba$^{133}$ | 7.2 y | 81 | 0.33% | Au |
| La$^{138}$ | $10^{11}$ y | 81 | 0.33% | Au |
| Te$^{121i}$ | 140. d | 81.9 | 1.45% | Au |
| Pt$^{191}$ | 3.0 d | 82.5 | 2.16% | Au |
| Po$^{206}$ | 8.8 d | 82.9 | 2.64% | Au |
| Pb$^{211}$ | 36. m | 83. | 2.75% | Au |
| Dy$^{157}$ | 8.2 h | 83.1 | ? | Hg |
| Gd$^{153}$ | 230 d | 83.3 | 0.23% | Hg |
| Cd$^{104}$ | 59.2 m | 83.5 | 0.47% | Hg |
| Kr$^{79}$ | 1.44 d | 84.0 | 1.1% | Hg |
| Tn$^{231}$ | 10.7 d | 84.1 | 1.2% | Hg |
| Tm$^{170}$ | 129. d | 84.23 | 1.33% | Hg |
| Tc$^{170}$ | 127. d | 84.3 | 1.4% | Hg |
| Ra$^{224}$ | 3.64 d | 84.3 | 1.4% | Hg |
| Tn$^{228}$ | 1.91 y | 84.4 | 1.5% | Hg |
| Ta$^{182}$ | 111. d | 84.667 | 1.8% | Hg |
| Re$^{182}$ | 3.0 h | 84.67 | 1.85% | Hg |
| Re$^{183}$ | 125. d | 84.7 | 1.9% | Hg |
| Ta$^{183}$ | 5.2 d | 84.7 | 1.9% | Hg |
| Ac$^{225}$ | 10. d | 85. | 2.2% | Hg |
| Pb$^{81i}$ | 31.5 m | 85 | 2.2% | Hg |
| Nd$^{151}$ | 12. m | 85.4 | 2.7% | Hg |
| Br$^{77}$ | 2.4 d | 86. | 0.56% | Tl |
| As$^{77}$ | 38.9 h | 86. | 0.56% | Tl |
| Te$^{160}$ | 72.3 d | 86. | ? | Tl |
| Eu$^{155}$ | 1.8 y | 86.4 | 0.99% | Tl |
| Ho$^{161i}$ | 56.3 h | 86.4 | 0.99% | Tl |
| Pa$^{233}$ | 27.2 d | 86.66 | 1.25% | Tl |
| Tb$^{160}$ | 73.1 d | 86.7 | 1.36% | Tl |
| Th$^{233}$ | 22.1 m | 86.9 | 1.59% | Tl |
| La$^{142}$ | 77. m | 87. | 1.7% | Tl |
| Pd$^{109}$ | 13.6 h | 87. | 1.7% | Tl |
| Cd$^{109}$ | 470. d | 87.6 | 2.43% | Tl |
| Er$^{171}$ | 36.7 m | 88.0 | ? | Pb |
| Pb$^{214}$ | 26.8 m | 88.4 | 0.45% | Pb |
| Te$^{123i}$ | 112. d | 88.63 | 0.71% | Pb |
| Te$^{127i}$ | 103. d | 88.67 | 0.76% | Pb |
| Eu$^{156}$ | 14.7 d | 88.9 | 1.0% | Pb |
| Lu$^{176}$ | $2.4 \times 10^{10}$ y | 88.9 | 1.0% | Pb |
| Sb$^{120i}$ | 5.9 d | 89. | 1.1% | Pb |
| Eu$^{145}$ | 5.0 d | 89. | 1.1% | Pb |
| Tb$^{156}$ | 5.16 d | 89.1 | 1.2% | Pb |
| Hf$^{175}$ | 7.0 d | 89.4 | 1.52% | Pb |
| Ge$^{69}$ | 1.63 d | 90.0 | 2.2% | Pb |
| Dy$^{155}$ | 10. h | 90.28 | 2.3% | Pb |
| Ho$^{164i}$ | 36.7 m | 90.6 | 0.087% | Bi |
| Lu$^{171}$ | 1.64 y | 90.6 | 0.087% | Bi |
| Lu$^{172}$ | 6.7 d | 90.6 | 0.087% | Bi |
| Bi$^{204}$ | 12.0 h | 90.9 | 0.42% | Bi |
| At$^{209}$ | 5.5 h | 90.95 | 0.47% | Bi |
| Nd$^{147}$ | 11.4 d | 91.26 | 0.81% | Bi |
| Ba$^{131}$ | 11.5 d | 92.0 | 1.6% | Bi |
| Ta$^{182}$ | 118. d | 92.0 | 1.6% | Bi |
| Er$^{169i}$ | 105. d | 92.1 | 1.7% | Bi |
| Th$^{234}$ | 24.3 d | 92.13 | 1.7% | Bi |
| Cu$^{67}$ | 2.44 d | 92.2 | 1.8% | Bi |
| Ga$^{67}$ | 3.25 d | 92.3 | 1.9% | Bi |
| Kr$^{76}$ | 9.7 h | 93.0 | 2.7% | Bi |
| Ag$^{111}$ | 7.54 d | 93.0 | 2.7% | Bi |
| Ta$^{182}$ | 111. d | 93.0 | 2.7% | Bi |
| Hf$^{81i}$ | 5.4 h | 93.3 | 3.0% | Bi |
| Cd$^{107}$ | 6.74 d | 93.5 | 3.2% | Bi |
| Yb$^{169i}$ | 30.9 d | 93.64 | 3.3% | Bi |
| Dy$^{165}$ | 2.3 h | 94.79 | 4.5% | Bi |
| Cr$^{48}$ | 23. h | 116.0 | 0.35% | U |
| Tl$^{200}$ | 26.5 h | 116.5 | 0.78% | U |
| Pb$^{198}$ | 2.3 h | 116.9 | 1.1% | U |
| Mn$^{56}$ | 2.6 h | 117. | 1.2% | U |
| U$^{234}$ | $2.5 \times 10^5$ y | 117.5 | 1.6% | U |
| Ga$^{65i}$ | 15.2 m | 118. | 2.0% | U |
| Yb$^{167}$ | 18.5 m | 118. | 2.0% | U |
| Yb$^{177}$ | 1.88 h | 119. | 2.9% | U |

I claim:

1. Apparatus for the diagnosis of body structures into which an essentially monochromatic gamma-emitting radioactive isotope has been introduce, wherein said gamma-emitting radioactive isotope emits gamma photons at a specific energy and wherein some of said gamma photons lose energy due to Compton scattering in said body structures so that on emerging from said body structures they have second energies below said specific energy, the apparatus comprising, in sequence, a collimator through which photons emanating from the body structure being studied are directed; a first position sensitive photon detector, said first photon detector being adapted to absorb a fraction lying between 10 and 50% of both the scattered and non-scattered photons incident thereon; a filter comprising an element with an atomic number not less than 74 and having an absorption edge at an energy just below said specific energy but above said second energies, whereby said filter preferentially absorbs photons emanating from but not scattered within said body structures and preferentially transmits scattered photons; a second position sensitive photon detector positioned after said filter in line with said body structures, said first detector and said filter for detecting scattered photons passing through said filter and analysing means for producing an image due to non-scattered photons from the image of scattered photons formed by the second detector and the image of scattered and non-scattered photons formed by the first detector.

2. Apparatus in accordance with claim 1 wherein said first photon detector is a position sensitive gas detector.

3. Apparatus in accordance with claim 1, wherein said first photon detector is a position sensitive detector based on a liquid noble gas.

4. Apparatus in accordance with claim 1, wherein said second photon detector is a NaI scintillation crystal.

5. Apparatus in accordance with claim 1, wherein said first photon detector is a fast scintillation detector having a fast pulse decay time; wherein said second photon detector is a slow scintiallation crystal, wherein said filter is optically transparent and wherein said analysing means comprises a single set of photosensitive detectors positioned to detect light emitted from said slow scintillation crystal and light emitted from said fast scintillation crystal after passage of the light emitted by said fast scintillation crystal through said filter and said slow scintillation crystal.

6. Apparatus in accordance with claim 5, wherein said first photon detector is a CsI scintillation crystal, and said second photon detecto is a NaI scintillation crytal.

7. Apparatus in accordance with claim 5 wherein said single set of photodetectors comprises a single set of photomultipliers provided after said second detector.

8. Apparatus in accordance with.claim 5 wherein said analysing means comprises electronic circuit means for measuring the pulse decay time and for determining therefrom in which of said photon detectors incident photons are stopped.

9. Apparatus in accordance with claim 8, said apparatus further comprising means for feeding information from said circuit means for measuring the pulse decay time to circuit means for measuring the pulse height.

10. Apparatus in accordance with claim 8 and wherein said analysing means includes position localizing circuitry which also receives signals from said electronic circuit means for determining pulse decay time.

11. Apparatus in accordance with claim 5 wherein said fast pulse decay time is not more than 100 nsec.

12. Apparatus in accordance with claim 5, wherein said first photon detector is a CsF scintillation crystal, and said second photon detector is a NaI scintillation crystal.

13. Apparatus in accordance with claim 5, wherein said first photon detector is a BaF scintillation crystal, and said second photon detector is a NaI scintillation crystal.

14. Apparatus in accordance with claim 1 wherein said analysing means includes a computer to store and process signal information.

* * * * *